(12) United States Patent
DeGasparo et al.

(10) Patent No.: US 10,131,543 B2
(45) Date of Patent: Nov. 20, 2018

(54) METHOD FOR PRODUCING POROUS CALCIUM DEFICIENT HYDROXYAPATITE GRANULES

(71) Applicants: Bioventus, LLC, Durham, NC (US); Mathys AG Bettlach, Bettlach (CH)

(72) Inventors: Alex DeGasparo, Biel (CH); Noemie Van Garderen, Dubendorf (CH); Marc Bohner, Grenchen (CH); Howard Seeherman, Cambridge, MA (US); Eric Vanderploeg, Stoneham, MA (US)

(73) Assignees: Bioventus, LLC., Durham, NC (US); Mathys AG Bettlach (CH)

( * ) Notice: Subject to any disclaimer, the term of this patent is extended or adjusted under 35 U.S.C. 154(b) by 0 days.

(21) Appl. No.: 15/321,297

(22) PCT Filed: Jun. 23, 2014

(86) PCT No.: PCT/CH2014/000085
§ 371 (c)(1),
(2) Date: Dec. 22, 2016

(87) PCT Pub. No.: WO2015/196306
PCT Pub. Date: Dec. 30, 2015

(65) Prior Publication Data
US 2017/0158510 A1 Jun. 8, 2017

(51) Int. Cl.
*C01B 25/32* (2006.01)
*A61K 47/02* (2006.01)

(52) U.S. Cl.
CPC ............ *C01B 25/32* (2013.01); *A61K 47/02* (2013.01); *C01P 2004/61* (2013.01); *C01P 2006/16* (2013.01)

(58) Field of Classification Search
CPC ..... C01B 25/32; A61K 47/02; C01P 2004/61; C01P 2006/16
See application file for complete search history.

(56) References Cited

U.S. PATENT DOCUMENTS 5,462,722 A 10/1995 Liu et al.

FOREIGN PATENT DOCUMENTS

| JP | H07-206412 A | 8/1995 |
| JP | 2000-302567 A | 10/2000 |

(Continued)

OTHER PUBLICATIONS

Legeros et al., "Biphasic calcium phosphate bioceramics: preparation, properties and applications," Journal of Materials Science: Materials in Medicine 14 (2003) 201-209.

(Continued)

*Primary Examiner* — Anthony J Zimmer
(74) *Attorney, Agent, or Firm* — Kacvinsky Daisak Bluni PLLC; Judith Toffenetti

(57) ABSTRACT

The method is for producing porous calcium deficient hydroxyapatite granules and comprises the following steps: (a) subjecting granules of calcium sulfate anhydrous (CSA), calcium sulfate dihydrate (CSD) or calcium sulfate hemihydrate (CSH), the granules comprising interconnected pores with a minimum mean diameter of 3 microns, to a first incubation in an alkaline aqueous solution having a pH-value of less than 10 and containing $PO_4^{3-}$ ions; (b) subjecting the granules to a second incubation in an alkaline aqueous solution having a pH-value of more than 10 and optionally $PO_4^{3-}$ ions; (c) filtering and drying the obtained porous granules of calcium deficient hydroxyapatite; and wherein (d) the sum of the amounts of $PO_4^{3-}$ ions present in the first and second incubation is at least as large as the amount of $SO_4^{2-}$ ions of the granules used for step (a). The porous calcium deficient hydroxyapatite granules obtained by the invention may be purposefully used as carriers for biologically active substances in particular for proteins.

15 Claims, 5 Drawing Sheets

(56) References Cited

FOREIGN PATENT DOCUMENTS

| JP | H03-097610 A | 4/2003 | |
|---|---|---|---|
| JP | 2004-284890 A | 10/2004 | |
| JP | 2010-090014 A | 4/2010 | |
| KR | 2012 0073647 A | 7/2012 | |
| LV | 14492 B | 7/2012 | |
| RU | 2 395 476 C1 | 7/2010 | |
| WO | WO-2014141287 A1 * | 9/2014 | ......... A61K 41/0033 |

OTHER PUBLICATIONS

Suwanprateeb et al. "Low temperature preparation of calcium phosphate structure via phosphorization of 3D-printed calcium sulfate hemihydrate based material", Journal of Materials Science: Materials in Medicine, vol. 21, No. 2, pp. 419-429, 2009.
Sachiko et al. "Porous hydroxyapatite monoliths from gypsum waste", Journal of Materials Chemistry, vol. 8, No. 12, pp. 2803-2806, 1998.
International Search Report and Written Opinion of PCT/CH2014/000085; dated Mar. 18, 2015, 12 pages.
Translation of Japanese Office Action dated Jul. 25, 2018, co-pending JP Application No. 2017-519738, 4 pages.

* cited by examiner

METHOD FOR PRODUCING POROUS CALCIUM DEFICIENT HYDROXYAPATITE GRANULES

CROSS-REFERENCE TO RELATED APPLICATION

This application is a national stage filing, under 35U.S.C. § 371, and claims the priority of PCT/CH2014/000085, filed Jun. 23, 2014; the contents of which are hereby incorporated by reference.

BACKGROUND OF THE INVENTION

1. Field of the Invention

The invention relates to a method for producing porous calcium deficient hydroxyapatite granules according to the preamble of claim 1 and porous calcium deficient hydroxyapatite granules according to the preamble of claim 39.

2. Description of the Related Art

From U.S. Pat. No. 5,462,722 Liu et al. a method for converting a particle of calcium sulfate is known which comprises a single incubation step for said particle of calcium sulfate in a preheated aqueous alkaline solution of a phosphate salt having a pH of at least 10. Liu et al. is silent to the presence and therefore to the dimensions of any pores of the calcium sulfate granules before their single incubation. Liu et al. does not disclose any information about the microstructure of the granules.

BRIEF SUMMARY OF THE INVENTION

It is an object of the invention to provide a method for producing porous calcium deficient hydroxyapatite granules with a predetermined microstructure making them particularly useful as carriers for biologically active substances. A further object of the invention is to provide porous calcium deficient hydroxyapatite granules comprising a plurality of micropores with a minimum mean diameter of 3 microns and being interconnected by channels having a mean diameter larger than 1 micron.

The invention solves the posed problem with a method comprising the features of claim 1, and with porous calcium deficient hydroxyapatite granules comprising the features of claim 39.

DEFINITIONS

CSH

Calcium sulfate hemihydrate ($CaSO_4 \cdot 1/2\ H_2O$). It can be an alpha-CSH or a beta-CSH. alpha-CSH is obtained from CSD by hydrothermal conditions (ex: autoclave) and beta-CSH is obtained by drying CSD (e.g. at about 120° C.).

CSA

Calcium sulfate anhydrous ($CaSO_4$). It exists 3 types: gamma-CSA (obtained from about 150 to 300° C.), beta-CSA (obtained at temperature higher than 300° C.), alpha-CSA (obtained at temperature higher than 1180° C.).

CSD

Calcium sulfate dihydrate ($CaSO_4 \cdot 2H_2O$).

CDHA

Is any hydroxyapatite with the general formula $Ca_{(10-x)}(PO_4)_{(6-x)}(HPO_4)_x(OH)_{(2-x)}$ where x is larger than 0 (max: 2).

SSA is the specific surface area

The method according to the invention allows the production of porous calcium deficient hydroxyapatite granules with a high specific surface area. This parameter is of importance when the granules according to the invention are used as carriers for biologically active substances in particular for proteins.

The first incubation aims at converting calcium sulfate into calcium phosphate. The second incubation has two purposes: (i) clean the granules from unwanted ionic species (e.g. ammonium) and (ii) increase the residual pH value of the granules (this residual pH value can be determined by dipping the granules into demineralized water)

The second incubation of the method according to the invention allows the increase in pH of granules residue and to transform the eventual remained CSA to CDHA according to the equation: $9\ CaSO_4 + 9\ (NH_4)_2HPO_4 + 6\ NaOH \rightarrow Ca_9(HPO_4)(PO_4)_5OH + 9\ (NH_4)_2SO_4 + 3\ Na_2HPO_4 + 5\ H_2O$ Further advantageous embodiments of the invention can be commented as follows:

In a special embodiment only granules of calcium sulfate anhydrous (CSA) are used in step (a).

Further the alkaline aqueous solution of step (a) can comprise either $(NH_4)(H_2PO_4)$, $(NH_4)_2(HPO_4)$, or $(NH_4)_3(PO_4)$ and either NaOH or KOH.

In a further embodiment the alkaline aqueous solution of step (b) can comprise NaOH or KOH. The function thereof is to neutralize phosphoric acid and to enhance the increase in SSA value and phase conversion.

In a further embodiment the liquid to powder ratio in the first incubation of step (a) is at most 15 ml/g, preferably at most 10 ml/g. In a further embodiment the liquid to powder ratio in step b) is lower than or equal to 15 ml/g, preferably lower or equal to 10 ml/g.

In a further embodiment the first incubation of step (a) and/or the second incubation of step (b) is performed at a temperature from 60° C. to 100° C. and preferably between 70° C. and 90° C.

In a further embodiment the granules are filtered and washed with water after the first incubation of step (a).

Further the granules may be filtered and washed with water after the second incubation of step (b).

In a further embodiment the porous granules of calcium sulfate anhydrous (CSA), calcium sulfate dihydrate (CSD) or calcium sulfate hemihydrate (CSH) are obtained by a spray drying process. The spray drying process can be controlled so as to produce spherical granules with a mean diameter below 200 μm.

In a further embodiment the porous granules of CSA, CSH, or CSD are obtained by first solidifying a slurry consisting of a mixture of CSA, CSH, or CSD powder and an aqueous or non-aqueous solution, and second breaking the resulting block into granules. The solidification process can be chosen from:

(i) drying, preferably by capillary forces;
(ii) gluing, preferably by using additives with gluing properties;
(iii) a cementing reaction when using CSH with an aqueous solution; or
(iv) freezing followed by freeze-drying, preferably in liquid nitrogen.

In a further embodiment a binder is used in the solidification process.

The CSA, CSD or CSH porous granules may be shaped with a high shear mixer and calcined. The CSA, CSD or CSH porous granules may be shaped by extrusion and followed by spheronization, preferably using microcrystalline cellulose.

In a further embodiment an additional sintering step is performed before or after the granulation step of claim 12 in the range of 650° to 1100° C., preferably between 680° and 800° C. The dwell time for the additional sintering step should preferably not be longer than 1 hour.

In a further embodiment a porogenic agent is used for obtaining the pores in the granules for step a). The porogenic agent may comprise particles having a mean diameter in the range of 1 to 700 micrometers. This allows obtaining interconnected pores in the granules of calcium sulphate anhydrous (CSA), calcium sulfate dihydrate (CSD) or calcium sulfate hemihydrate (CSH), as well as to reduce the risk of forming a dense CDHA core within the CDHA granules.

The porogenic agent my comprise particles having a mean diameter in the range of 3 and 20 micrometers. Alternatively the porogenic agent may comprise particles having a mean diameter in the range of 100 and 500 micrometers.

The porogenic agent can be made of a fully combustible material.

Further the porogenic agent may be removed by dissolution, preferably by a solvent debinding method. The solvent debinding method can be followed by a thermal step to finish the decomposition or to allow the sintering of the matrix and to increase the mechanical strength). Supercritical debinding can also be used.

The porogenic agent should preferably comprise less than 50 ppm of heavy metals. The porogenic agent may be a polysaccharide and preferably be selected from the following group of materials: flour, sugar, starch, carboxymethylcellulose, cellulose. The porogenic agent may be a polyol, and preferably be selected from the following group of materials: mannitol, polyethylene glycol, poly-(2-ethyl-2-oxazoline), polyvinyl alcohol.

The porogenic agent may be used in an amount of at least 0.5 weight-%, preferably at least 10 weight-% of the solid content comprising the calcium sulfate and the porogenic agent. The porogenic agent may be used in an amount of at most 60 weight-%, preferably at most 40 weight-%, preferably at least 10 weight-% of the solid content comprising the calcium sulfate and the porogenic agent.

In a further embodiment a foaming agent is used for obtaining the pores in the granules for step a).

In a further embodiment hydrogen peroxide is used for obtaining the pores in the granules for step a).

In a further embodiment the first and/or second incubation comprises stirring of the granules in the solution.

In a further embodiment the drying of the obtained granules after full conversion into CDHA comprises a heating step at a temperature higher than 60° C., preferably between 60° C. and 100° C. Full conversion means that more than 95% of the granules contain CDHA, the rest being CSA, DCPD (brushite; $CaHPO_4 \cdot 2H_2O$), and/or DCP (monetite; $CaHPO_4$).

In a further embodiment the porosity of the granules measured before the first incubation is larger than 40%, preferably larger than 50%.

Preferably the sum of the amounts of $PO_4^{3-}$ ions present in the first and second incubation is at least two times larger than the amount of $SO_4^{2-}$ ions in the granules.

In a further embodiment the CDHA granules are larger than 50 micrometers in diameter. Preferably the CDHA granules are smaller than 3000 micrometers in diameter In a further embodiment the granules of calcium sulfate anhydrous (CSA), calcium sulfate dihydrate (CSD) or calcium sulfate hemihydrate (CSH) used in step (a) comprise less than 1 weight-%, preferably less than 0.2 weight-% of carbon residues.

The invention refers also to porous calcium deficient hydroxyapatite granules characterized in that a) the granules comprise a plurality of micropores with a minimum mean diameter of 3 microns; and b) the micropores are interconnected by channels having a mean diameter larger than 1 micron.

In a special embodiment the granules comprise a plurality of micropores with a mean diameter of less than 20 microns. Preferably the granules have a SSA higher than 30 $m^2/g$, more preferably higher than 50 $m^2/g$.

Preferably the granules have a SSA lower than 120 $m^2/g$. Because the granules are aimed to be used as a protein carrier, a high specific surface area will enhance the presence of protein on the surface. A high value (higher than 30 $m^2/g$) is obtained—compared to beta-TCP—because no heat treatment at high temperature has to be performed, which would lead to a decrease in SSA value.

In a further embodiment the granules have a composition corresponding to $Ca_{(10-x)}(PO_4)_{(6-x)}(HPO_4)_x(OH)_{(2-x)}$ where x can vary from 0 to 2.

Preferably the granules have a Ca:P ratio in the range of 1.51 to 1.59.

In a further embodiment the porous granules are obtained by sintering the porous calcium deficient hydroxyapatite granules at a temperature larger than 600° C. to transform calcium-deficient hydroxyapatite in biphasic calcium phosphate. Biphasic calcium phosphate is a mixture of β-tricalcium phosphate and hydroxyapatite.

The porous granules may be obtained by sintering the porous calcium deficient hydroxyapatite granules at a temperature smaller than 1000° C. to transform calcium-deficient hydroxyapatite in biphasic calcium phosphate.

The porous calcium deficient hydroxyapatite granules obtained by the invention may be purposefully used as carriers for biologically active substances in particular for proteins.

A BRIEF DESCRIPTION OF THE DRAWINGS

Several embodiments of the invention will be described in the following by way of example and with reference to the accompanying drawings in which.

DETAILED DESCRIPTION OF THE INVENTION

Figure 1:
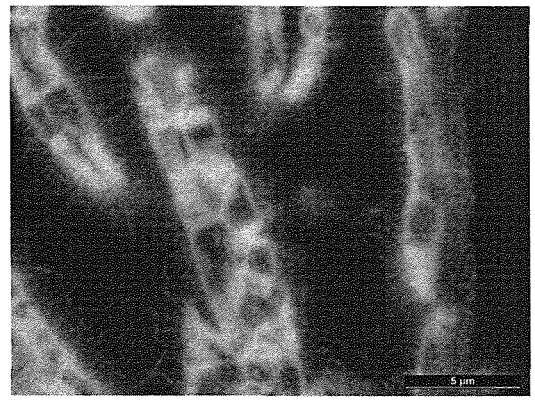
FIG. 1 illustrates the formation of a fibrillar layer surrounding the structure after the second incubation of granules from Example 2.

The following examples clarify the invention further in more detail.

A) Examples Devoted to the Synthesis of Calcium Sulfate Granules

EXAMPLE 1

300 g of CSD (d50: 22±18 μm) were mixed for 5 minutes with 280 ml demineralized water, 120 g corn starch (d50: 12±4 μm) and 8.4 g Duramax B-1000 until suitable viscosity of the slurry was obtained. This slurry was poured into a rectangular form and dried at 80° C. in a drying cupboard for 48 hours. The material was then pre-crushed with a hammer and a chisel to a size of about 2×2×2 cm before heat treatment at 750° C. in air to allow decomposition of the organics and sintering. β-CSA phase was then obtained. A jaw crusher was used to obtain the suitable granules size. A porosity of 60±2% was reached for the CSA granules.

EXAMPLE 2

90 g of γ-CSA (obtained by drying CSD during 16 h at 160° C.) were mixed in a Turbula mixer with 5.6 g stearic acid and 100 g pore formers (50 g polyethylene glycol (size between 200-400 μm) and 50 g of mannitol (size between 5-30 μm)). The powders were poured in a form and pressed up to 200 bar. The resulting form was then pre-crushed with a hammer and a chisel to a size of about 2×2×2 cm and heat treated at 800° C. A jaw crusher was then used to obtain the suitable β-CSA granules size. After incubation, a porosity of 50+/−7% and a pore size of 2 to 350 μm were obtained, as determined by image analysis of materialography sections.

EXAMPLE 3

12 g of α-CSH (obtained by autoclaving CSD at 120° C. during 1 h) was mixed manually with 6 g of corn starch (d50: 12±4 μm), while 50 g of paraffin and 4 drops of span 85 were mixed with a propeller. 8 mL of 0.01 M $CaSO_4$ was then poured onto the powders and mixed with the propeller; the paraffin+span 85 mixture was then added. The resulting paste was stirred at 1000 RPM until the suitable droplet size was obtained. The droplets were incubated 1 h30 to allow the conversion of CSH into CSD and the concomitant droplet hardening. The granules (=hard droplets) were then washed with 30 mL of petroleum spirit and filtered. These steps were repeated until a sufficient granule amount was obtained. Granules were then heat treated at 800° C. and β-CSA phase was obtained. Pore sizes and porosity were determined to be between 5 and 30 μm and 44 and 60%, respectively.

B) Examples Devoted to the Conversion of the Granules (Obtained in Examples 1 to 3) into CDHA.

EXAMPLE 4

A mixture of 188 mL of 4.4 M $(NH_4)_2HPO_4$ and 6 mL of 1.5 M NaOH (pH of the solution: 8.4) was pre-heated at 80° C. in a 500 mL closed container. Then, 50 g of β-CSA granules were added. The phosphate to sulfate molar ratio was about 2.2.

The granules were produced by one of the technique presented in Examples 1 to 3 but not exclusively. The granules were aged in the solution at 80° C. during 24 h with a slow rotation rate of 1 rpm to avoid granule fragmentation and agglomeration and were washed in several steps with in total 1 L water and filtered before starting the second incubation. 250 ml of 0.5 M NaOH (pH 13) was pre-heated at 80° C. before pouring the 50 g pre-converted granules into the solution and letting them aged at the same temperature during 24 h. Granules were washed with 1 L demineralized water, filtered and dried in a drying cupboard overnight at 80° C. This method allowed the production of granules composed of more than 95 wt. % CDHA with a specific surface area value higher than 30 $m^2/g$.

Microstructure of granules of Example 2 incubated such as in Example 4, with a size between 0.71 and 1.4 mm, was verified by impregnating the granules in a resin and polishing them.

Figure 2:
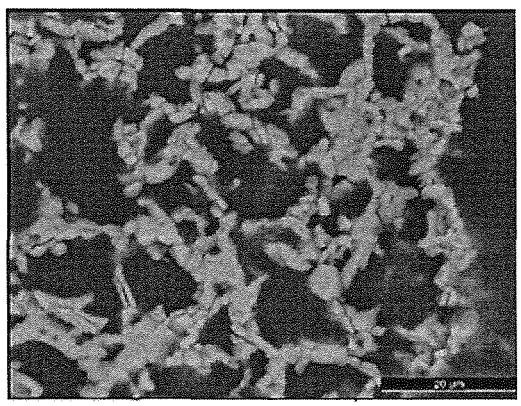
FIG. 2a shows the CSA microstructure.
FIG. 2b shows the CDHA microstructure with the formation of needles and the decrease in the pore size due to this phenomenon.
Figure 2B:
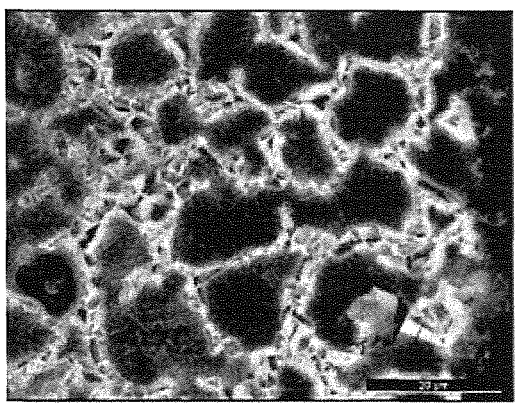

The SEM images shown in FIG. 1 and FIG. 2 reveal that the conversion of calcium sulfate results in the formation of a 1-2 μm thick porous coating on top of the initial calcium sulfate structure. In other words, calcium sulfate acts as template for the formation of CDHA. This explains also why the micropore interconnections of the calcium sulfate granules (=template) should be larger than 3 μm to prevent their closure during CDHA formation.

Figure 3:
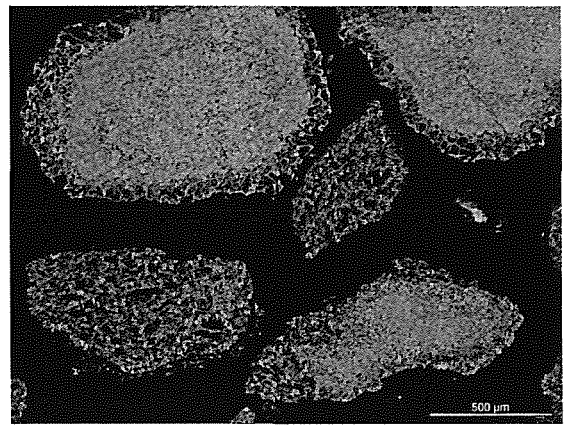
FIG. 3 shows the microstructure of the granules after the second incubation.

After the second incubation, the core of the granules appeared dense (FIG. 3), suggesting that the conversion from calcium sulfate to CDHA starts at the center of the granules.

Figure 4:
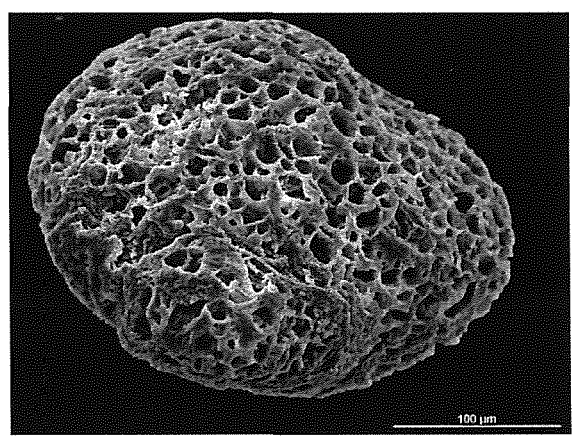
FIG. 4 shows the opening of the structure with 0.1 M HCl leaching

A highly interconnected microporosity can be obtained on the surface of the granules by incubating the granules in 0.1 M HCl for few minutes, preferably more than 5 minutes (FIG. 4).

EXAMPLE 5

The degree of conversion in Example 4 depends on the ratio between phosphate and sulfate ions. A faster conversion rate was observed with a higher ratio. Equivalent CDHA content can however be obtained with varying incubation time and temperature. The first incubation solution consisted of a mixture of 43 mL of 2 M $(NH_4)_2HPO_4$ solution and 2 mL of 0.5 M NaOH solution. This solution was used to incubate 50 g of granules in a 500 mL closed container under shaking. In these conditions, the phosphate to sulfate molar ratio was close to 0.8.

The granules were incubated either at 60° C. or 80° C. during 5 days. Granules were then washed with 500 mL demineralized water and filtered before starting the second incubation. The incubating solution was composed of 140 ml of 2 M $(NH_4)_2HPO_4$ and 6.5 ml of 0.5 M NaOH. The phosphate to sulfate ions ratio was about 0.2. The second incubation was performed under shaking at 60 or 80° C. and lasted 2 days. Washing and filtering steps were repeated. 250 mL of 0.5 M NaOH was then used as a third incubation step to neutralize the phosphoric acid released during the first 2 steps. This was performed at 80° C. during 15 hours. Washing and filtering steps were repeated and granules were allowed to dry at 80° C. overnight.

Figure 5A:
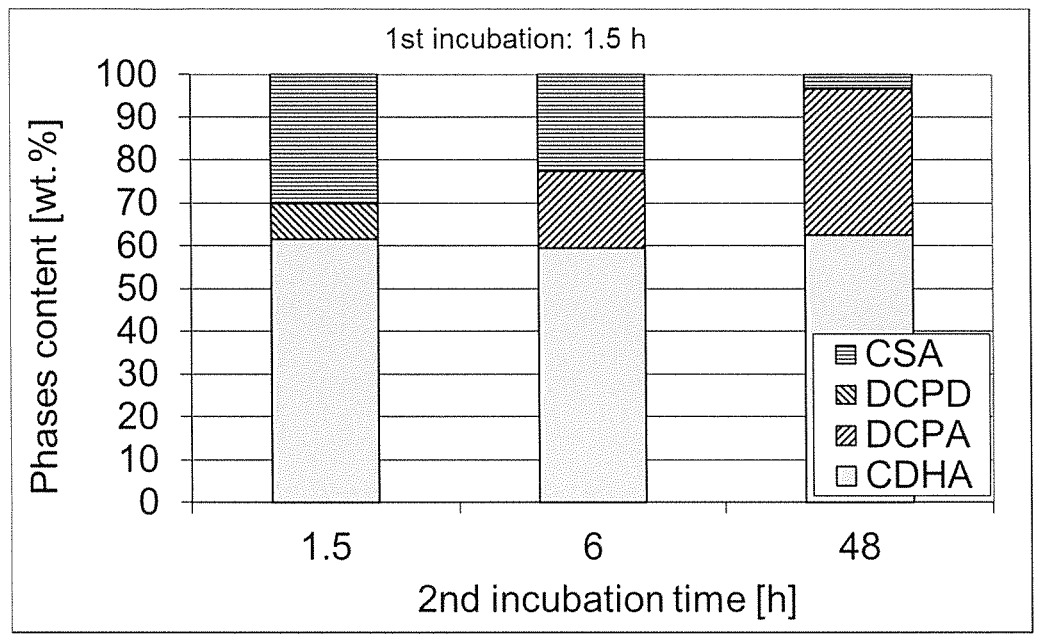
FIG. 5a shows the influence of NaOH incubation time (1.5, 6 and 48 h) after a $1^{st}$ incubation of 1.5 h
Figure 5B:
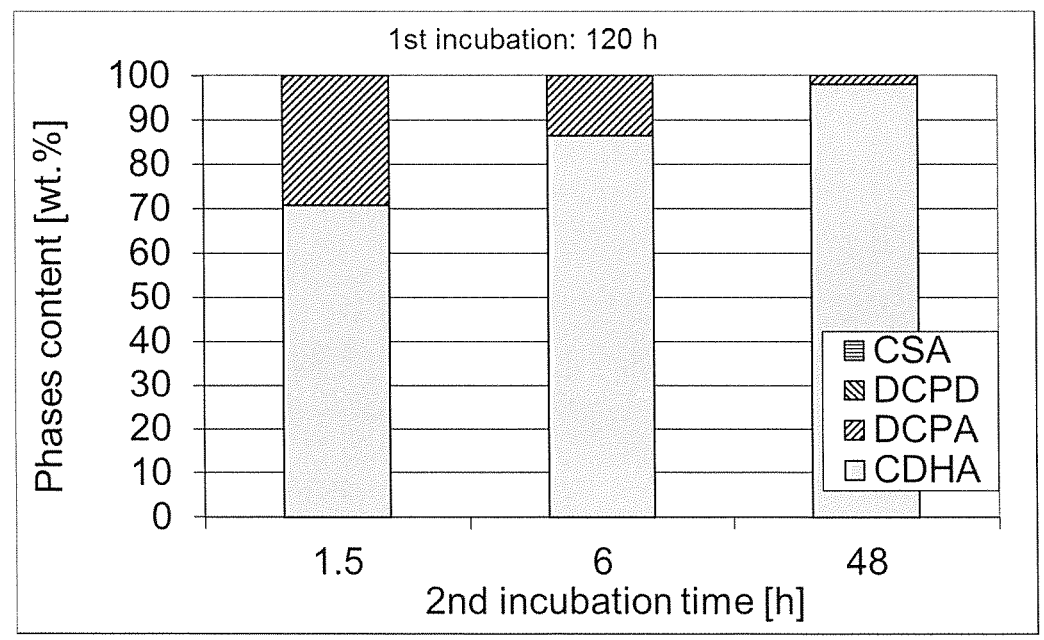
FIG. 5b shows the influence of NaOH incubation time (1.5, 6 and 48 h) after a $1^{st}$ incubation of 120 h.

FIG. 5 shows the effect of time on conversion. On FIG. 5-a) $1^{st}$ incubation was performed during 1.5 h, while on FIG. 5-b) it was performed during 5 days. A higher CDHA content was observed with longer $1^{st}$ incubation step, but also with longer $2^{nd}$ incubation step (FIG. 5-b).

Figure 6A:
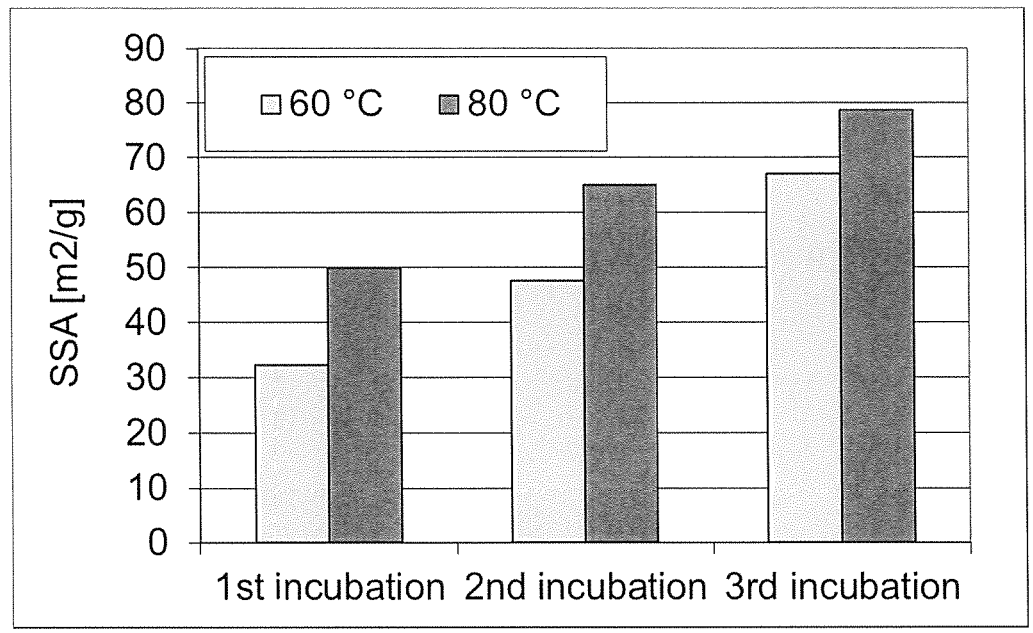
FIG. 6a shows the effect of incubation temperature on SSA values after each incubation step.
Figure 6B:
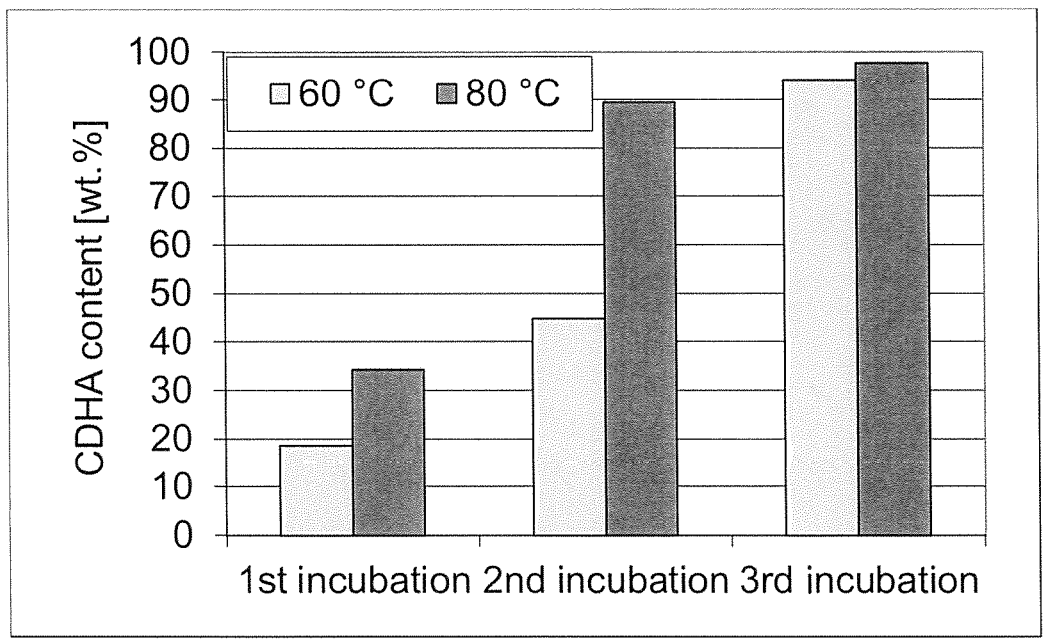
FIG. 6b shows the effect of incubation temperature on CDHA content after each incubation step.

Specific surface areas and CDHA content were verified for granules incubated at 60 and at 80° C. FIG. 6 shows that higher specific surface areas were obtained after incubation at 80° C., while CDHA conversion went faster.

Figure 7:
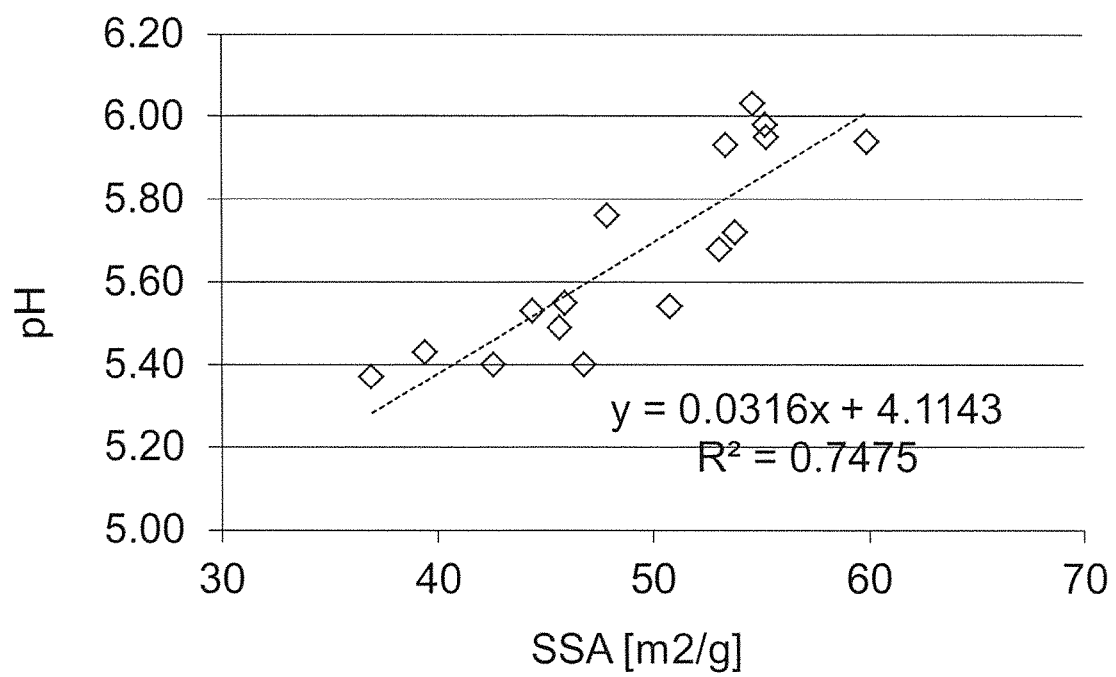
FIG. 7 shows the relation between the residual pH value of the granules and the SSA value

A relation between phase conversion and SSA value (between 30 and 120 m²/g) was determined, and between the residual pH of the granules and SSA value as represented in FIG. 7.

The pH of the granules residue was determined in a NaCl solution and was between 5 and 7 after the first incubation and between 7 and 11 after NaOH incubation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. Method for producing porous calcium deficient hydroxyapatite granules comprising the following steps:
   (a) subjecting granules of calcium sulfate anhydrous (CSA), calcium sulfate dihydrate (CSD) or calcium sulfate hemihydrate (CSH), the granules comprising interconnected pores with a minimum mean diameter of 3 microns, to a first incubation in an alkaline aqueous solution having a pH-value of less than 10 and containing $PO_4^{3-}$ ions;
   (b) subjecting the granules to a second incubation in an alkaline aqueous solution, said alkaline aqueous solution optionally comprising $PO_4^{3-}$ ions;
   (c) filtering and drying the obtained porous granules of calcium deficient hydroxyapatite; and wherein
   (d) the sum of the amounts of $PO_4^{3-}$ ions present in the first and second incubation is at least as large as the amount of $SO_4^{2-}$ ions of the granules used for step (a).

2. Method according to claim 1, wherein only granules of calcium sulfate anhydrous (CSA) are used in step (a).

3. Method according to claim 1, wherein the alkaline aqueous solution of step (a) comprises either $(NH_4)(H_2PO_4)$, $(NH_4)_2(HPO_4)$, or $(NH_4)_3(PO_4)$ and either NaOH or KOH.

4. Method according to claims 1, wherein the alkaline aqueous solution of step (b) comprises NaOH or KOH.

5. Method according to claim 1, wherein the liquid to powder ratio in the first incubation of step (a) is at most 15 ml/g.

6. Method according to claim 1, wherein the first incubation of step (a) and/or the second incubation of step (b) is performed at a temperature from 60° C. to 100° C.

7. Method according to claim 1, wherein the granules are filtered and washed with water after the first incubation of step (a).

8. Method according to claim 1, wherein the porous granules of CSA, CSH, or CSD are obtained by first solidifying a slurry consisting of a mixture of CSA, CSH, or CSD powder and an aqueous or non-aqueous solution, and second breaking the resulting block into granules.

9. Method according to claim 8, wherein the solidification process is selected from:
   (i) drying, capillary forces;
   (ii) gluing, using additives with gluing properties;
   (iii) a cementing reaction when using CSH with an aqueous solution; and
   (iv) freezing followed by freeze-drying.

10. Method according to claim 8, wherein an additional sintering step is performed before or after the granulation step of claim 8 in the range of 650° to 1100° C.

11. Method according to claim 10, wherein the dwell time for the additional sintering step is longer than 1 hour.

12. Method according to claim 9, wherein a porogenic agent is used for obtaining the pores in the granules for step a).

13. Method according to claim 12, wherein the porogenic agent comprises particles having a mean diameter in the range of 1 to 700 micrometers.

14. Method according to claim 8, wherein a foaming agent is used for obtaining the pores in the granules for step a).

15. Method according to claims 1, wherein the sum of the amounts of $PO_4^{3-}$ ions present in the first and second incubation is at least two times larger than the amount of $SO^{2-}$ ions in the granules.

* * * * *